United States Patent
Kumar et al.

(10) Patent No.: US 8,268,600 B2
(45) Date of Patent: *Sep. 18, 2012

(54) STRAIN AND A NOVEL PROCESS FOR ETHANOL PRODUCTION FROM LIGNOCELLULOSIC BIOMASS AT HIGH TEMPERATURE

(75) Inventors: Adhikari Dilip Kumar, Dehradun (IN); Sachin Kumar, Dehradun (IN); Sharma Chandra Dutt, Dehradun (IN); Deep Chand, Dehradun (IN)

(73) Assignee: Council of Scientific & Industrial Research, New Delhi (IN)

( * ) Notice: Subject to any disclaimer, the term of this patent is extended or adjusted under 35 U.S.C. 154(b) by 478 days.

This patent is subject to a terminal disclaimer.

(21) Appl. No.: 12/390,851

(22) Filed: Feb. 23, 2009

(65) Prior Publication Data

US 2009/0226993 A1 Sep. 10, 2009

(30) Foreign Application Priority Data

Mar. 5, 2008 (IN) ............................. 538/DEL/2008

(51) Int. Cl.
*C12P 7/06* (2006.01)
*C12P 7/10* (2006.01)

(52) U.S. Cl. ...................... 435/161; 435/165; 435/255.1

(58) Field of Classification Search .................. None
See application file for complete search history.

(56) References Cited

U.S. PATENT DOCUMENTS

| | | | |
|---|---|---|---|
| 4,094,742 A | 6/1978 | Bellamy | |
| 5,182,199 A | 1/1993 | Hartley | |
| 5,554,520 A | 9/1996 | Fowler et al. | |
| 5,580,389 A | 12/1996 | Farone et al. | |
| 5,820,687 A | 10/1998 | Farone et al. | |
| 7,285,403 B2 | 10/2007 | Jeffries et al. | |
| 7,344,876 B2 * | 3/2008 | Levine | 435/255.1 |

FOREIGN PATENT DOCUMENTS

| | | |
|---|---|---|
| WO | 2007053600 A2 | 5/2007 |
| WO | 2007130984 A2 | 11/2007 |

OTHER PUBLICATIONS

Ward et al., Appl Microbiol Biotechnol (1995) 43 : 408-411.*
Banat et al., Acta Biotechnol. 16 (1996) 2-3, 215-223.*
Anderson et al., (Applied and Environmental Microbiology, 1986, vol. 51, No. 6, p. 1314-1320.*
(Bioresour Technol. Dec. 2007;98(17):3367-74. Epub May 29, 2007.*
Lukondeh et al., J Ind Microbiol Biotechnol (2005) 32: 284-288.*

* cited by examiner

*Primary Examiner* — Irene Marx
(74) *Attorney, Agent, or Firm* — Luedeka Neely Group, PC

(57) ABSTRACT

The present invention relates to a novel thermophilic ethanol producing yeast strain, a microorganism, *Kluyveromyces* sp. IIPE453 MTCC 5314, classified as yeast, which exhibits growth and sugar fermentation at higher temperature range between 37° C. to 55° C. The novel yeast strain is capable of utilizing wide range of mono and di-saccharide sugars belongs to hexose and pentose carbohydrate family individually or in a mixture that obtained from hydrolysis of lignocellulosic biomass, such as sugarcane bagasse or starch based biomass such as cassava, potato, corn etc. for its growth and produce ethanol by fermentation process at temperature range 40° C. to 55° C. It also relates to a novel process for the preparation of ethanol by *Kluyveromyces* species IIPE453. Thus application of thermophilic yeast strain *Kluyveromyces* sp. IIPE453 MTCC 5314 has wide scope for industrial production of bioethanol from low cost renewable biomass as alternate feedstock to molasses.

8 Claims, 6 Drawing Sheets

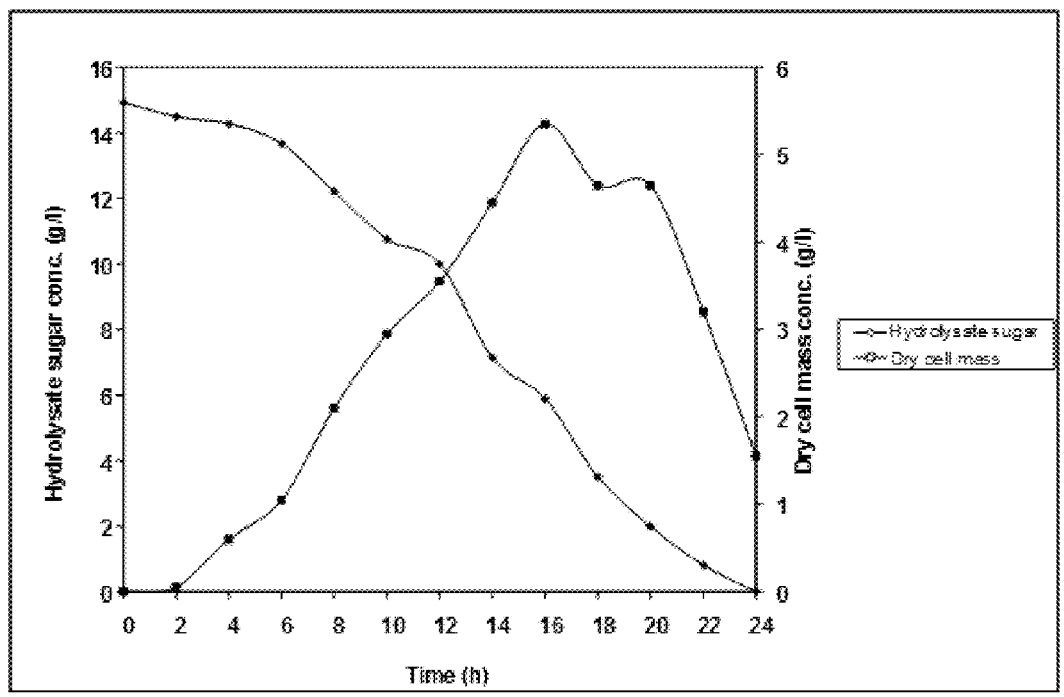
Figure 1: Growth of thermophilic yeast, *Kluyveromyces* sp. IIPE453, MTCC 5314, on xylose rich stream that obtained in first stage hydrolysis of sugar cane bagasse 45°C.

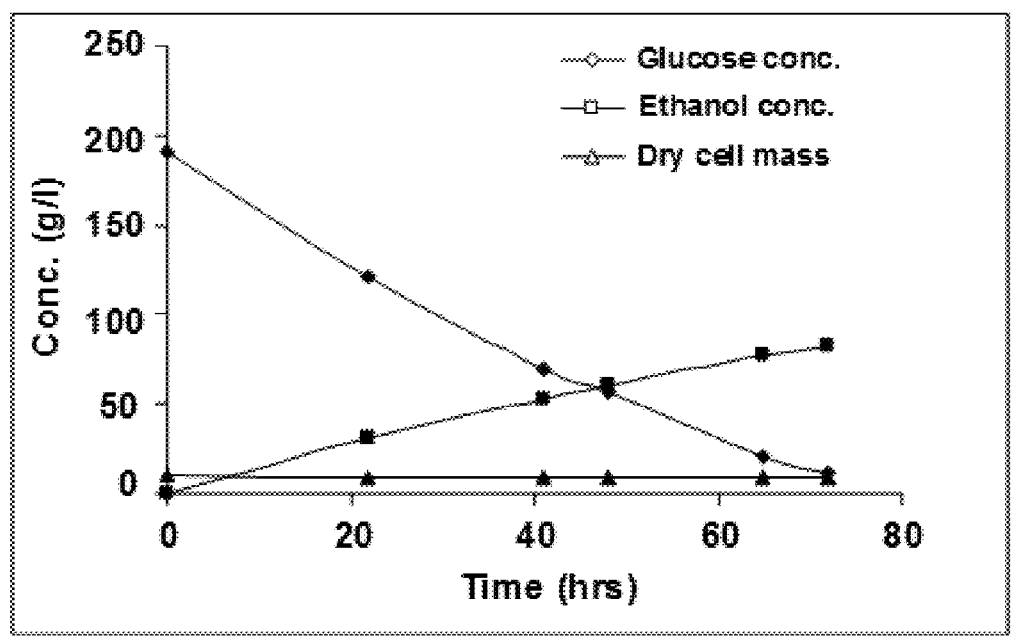
Figure 2: Batch fermentation on glucose at 45° C. by thermophilic yeast, *Kluyveromyces* sp. IIPE453, MTCC 5314.

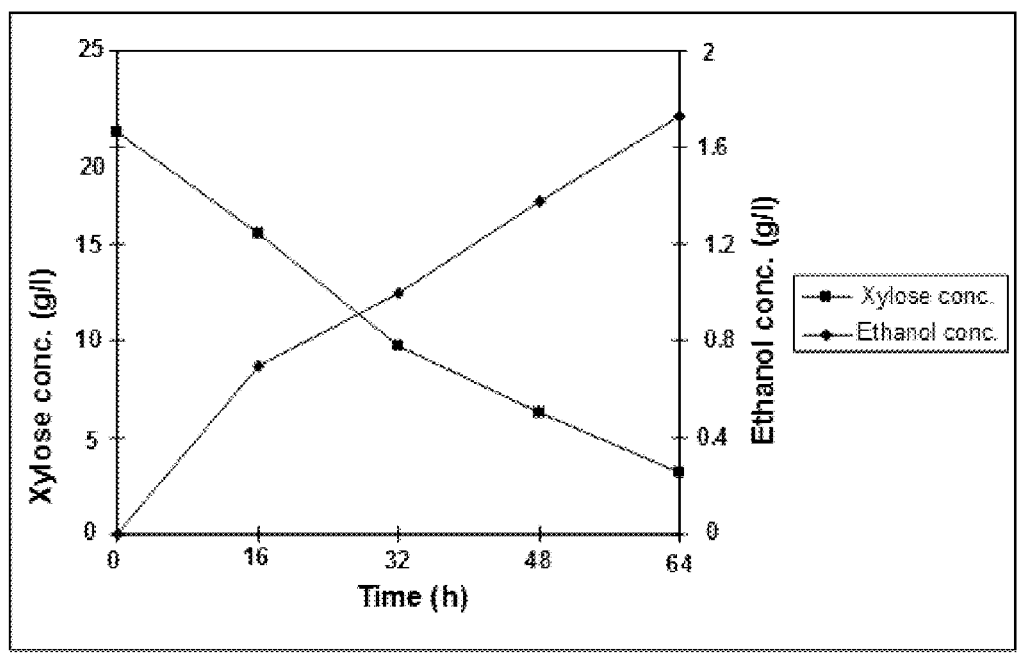
Figure 3: Batch fermentation on xylose at 45° C. by thermophilic yeast, *Kluyveromyces* sp. IIPE453, MTCC 5314.

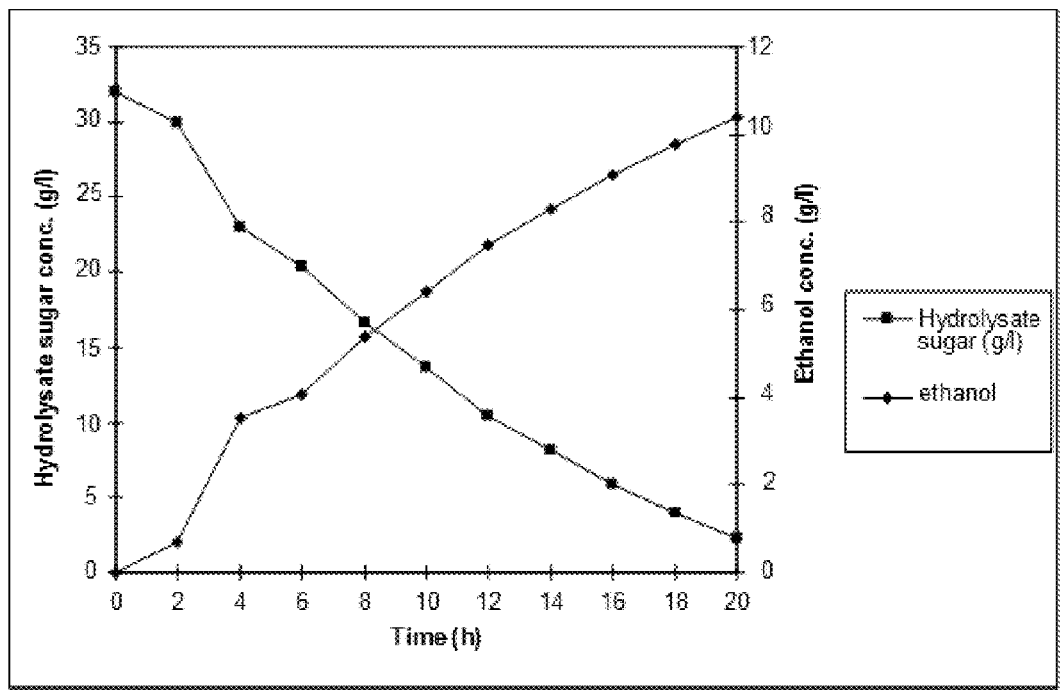
Figure 4: Batch fermentation on sugar cane bagasse hydrolysate at 50° C. by thermophilic yeast, *Kluyveromyces* sp. IIPE453, MTCC 5314.

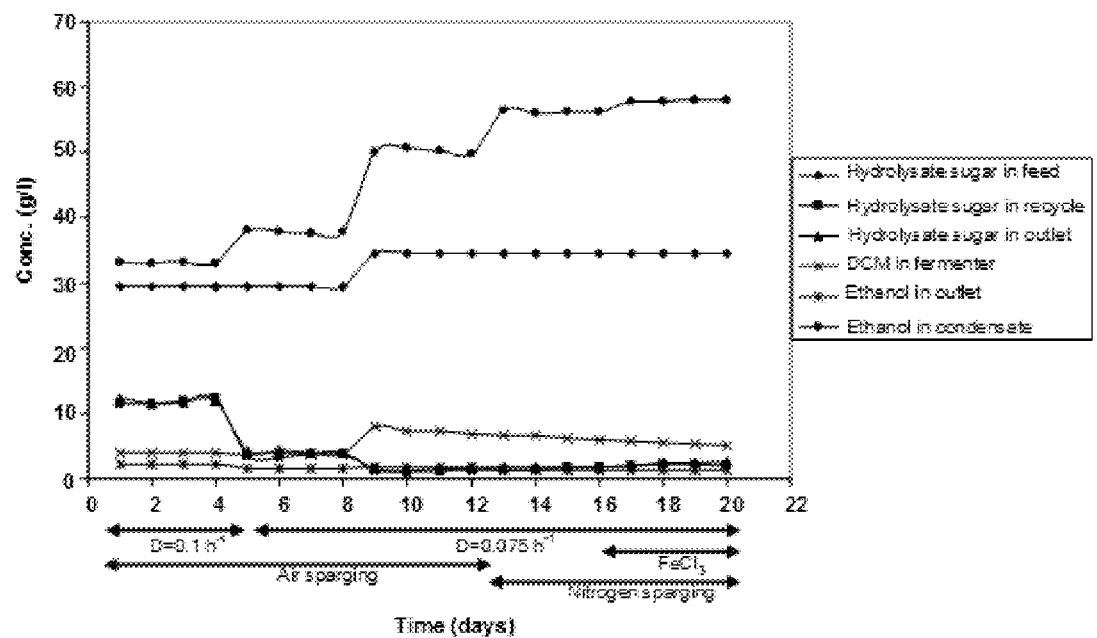
Figure 5: Continuous fermentation with cell recycle at 50° C. and air/gas stripping in sugarcane bagasse hydrolysate by thermophilic yeast, *Kluyveromyces* sp. IIPE453, MTCC 5314.

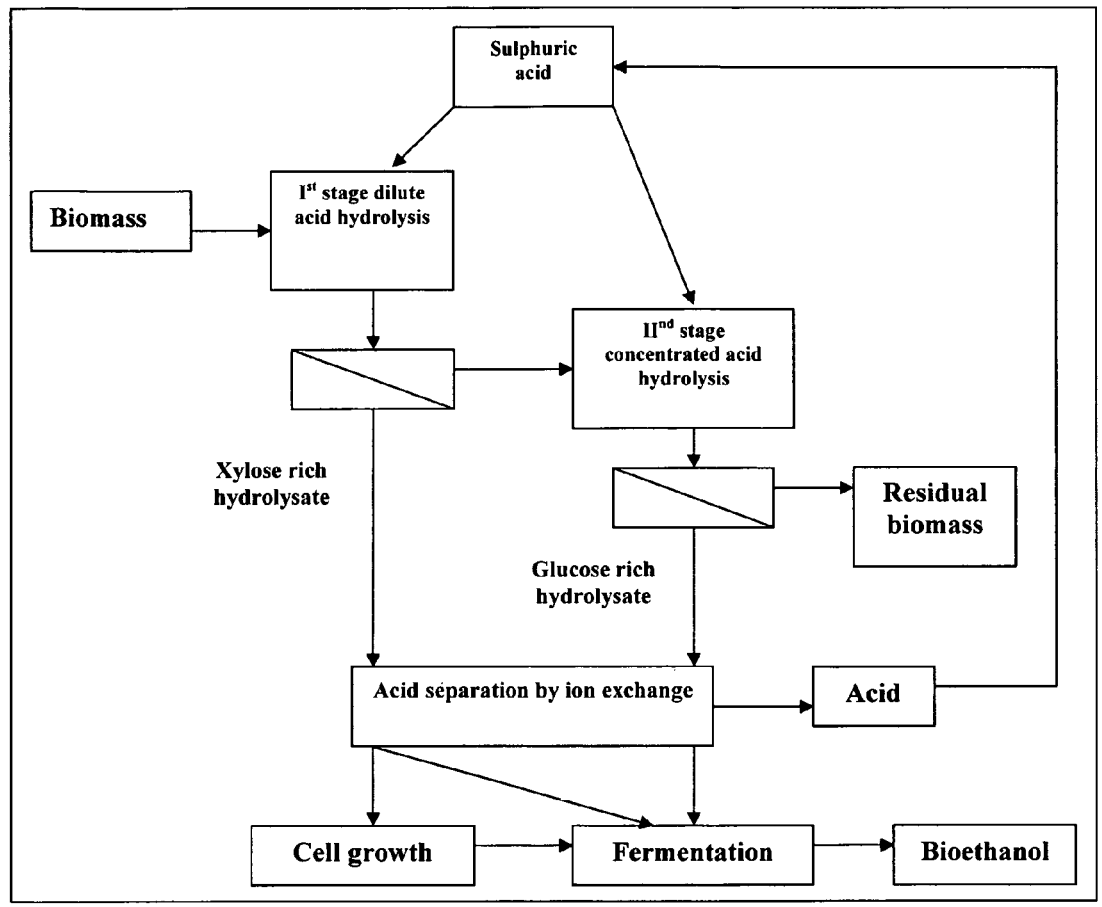
Figure 6: The flow diagram of the process from lignocellulosic biomass to ethanol production.

STRAIN AND A NOVEL PROCESS FOR ETHANOL PRODUCTION FROM LIGNOCELLULOSIC BIOMASS AT HIGH TEMPERATURE

FIELD OF INVENTION

The present invention relates to a novel strain and a novel process for ethanol production from lignocellulosic biomass at high temperature, wherein the process comprises the hydrolysis of lignocellulosic biomass to produce fermentable sugars, recovery of fermentable sugars from hydrolysate, fermentation of sugars to ethanol by thermophilic yeast, *Kluyveromyces* sp. IIPE453, MTCC 5314, which exhibits growth and sugar fermentation at high temperature range between 37-65° C. and in situ recovery of ethanol by air/gas stripping. *Kluvveromvces* sp. IIPE 453 was deposited in the Microbial Type Culture Collection & Gene Bank in Sector 39-A, Chandigarh—160 036 India on Oct. 27, 2006 under accession number MTCC 5314. The novel yeast strain is capable of utilizing wide range of mono and disaccharide sugars individually or in a mixture that are obtained from the hydrolysis of lignocellulosic biomass, such as sugarcane bagasse or starch based biomass such as cassaya, potato, corn etc. for its growth and produce ethanol by fermentation process at temperature range 40-65° C. The hydrolysis of lignocellulosic biomass is carried out in two stages. In first stage, mainly hemicellulose is hydrolyzed to xylose by dilute sulphuric acid treatment producing a xylose rich stream and in second stage residual bagasse is hydrolyzed to glucose rich stream by using concentrated sulphuric acid. At each stage the sugars are recovered from acid by ion exchange chromatography and acid is recycled for further hydrolysis. The part of xylose rich hydrolysate is used to grow the thermophilic yeast, *Kluyveromyces* sp. IIPE453, MTCC 5314 and the remaining part of xylose rich hydrolysate and total glucose rich hydrolysate are used for fermentation at the temperature range 40-55° C. in batch fermentation. The strain has capability to utilize both glucose and xylose simultaneously for growth and fermentation.

BACKGROUND OF THE INVENTION AND DESCRIPTION OF PRIOR ART

Bioethanol is being blended with gasoline 5-80% as transportation fuel in different countries to substantiate the rising price of crude oil and such high-octane blended fuel that reduces $CO_2$ and $NO_x$ emission from the automobiles.

Lignocellulosic biomass based ethanol production has many advantages. The large scale availability of biomass at a cheaper cost, environmentally benign bioprocessing to produce ethanol, national energy security, competitive alcohol based downstream chemicals, macroeconomic benefits for rural communities and the society at a large, has accelerated the biomass based bioethanol production worldwide. The lignocellulosic feed stock does not compete for food and land available for food production. Bioethanol as fuel is carbon neutral when produced from lignocellulosic biomass.

Application of thermophilic microorganisms that are capable of producing ethanol at higher temperature is highly demanded in the industry to reduce the cost of ethanol purification. Further, important advantages of using thermophilic microorganisms i.e.; bacteria and yeast at higher temperature include high rate of sugar metabolism, tolerance to high salt and solvent concentration, saving of energy on cooling of fermentation process and recovery of ethanol and significant restriction of contamination chances. Application of thermophilic yeast for ethanol production from different mono and disaccharides and carbohydrates would have advantages over thermophilic bacteria because of higher genetic stability and higher metabolic capacity as compared to bacteria.

Reference may be made to (Ghosh P and Ghose T K, Advanced Biochemical Engineering/Biotechnology, Vol 20, Biotechnology in India II, Scheper T (ed.) Springer, New York, 1-27, 2003) wherein bioethanol is being produced from molasses in India or from sugarcane juice in Brazil or from cereal grains in USA and Europe by fermentation process using yeast, *Saccharomyces cereviciae* or bacteria *Zymomonas mobilis* and other microorganisms in the temperature range of 28-35° C. The draw backs are the ethanol present in the fermented broth at low concentration (6-9%) is further purified to 99.9% by distillation, rectification, azeotropic distillation and dehydration process at temperature range of 70-100° C. with high input of energy which is a major process cost for ethanol production. The *Saccharomyces cereviciae* or bacteria *Zymomonas mobilis* are not capable of utilizing different mono and disaccharides except glucose and sucrose to ethanol limiting the scope of utilization of these microorganisms for ethanol production from lignocellulosic and starch biomass. The optimum temperature of growth and fermentation limits to 32-37° C. causing contamination problem. The microorganisms, *Saccharomyces cereviciae* and *Zymomonas mobilis* have low tolerance to ethanol concentration up to 8%.

Reference may be made to (Romero et al., Biochemical Engineering Journal, 36, 108-115, 2007) wherein ethanol fermentation of olive tree pruning hydrolysate with *Pachysolen tannophilus* has been reported with an ethanol yield of 0.38 g/g sugar in hydrolysate at 30° C. and pH 3.5. The conversion of the hemicellulose fraction was 92% in around 300 h. The draw backs are the substrate consumption rate and ethanol production rate are very slow. The strain utilizes only pentose sugars to ethanol, no hexose sugars utilization reported.

Reference may be made to (Cheng et al., Biotechnology Letters, 29, 1051-1055, 2007) wherein sugarcane bagasse hemicellulose hydrolysates has been fermented to ethanol using *Pachysolen tannophilus* DW06 giving 21 g/l ethanol; the yield being 0.35 g/g sugar and the productivity of 0.59 $g.l^{-1}.h^{-1}$ at 30° C. The draw backs are the strain utilizes only pentose sugars to ethanol, no hexose sugars utilization reported. The ethanol productivity is low.

Reference may be made to (Katahira et al., Applied Microbiology and Biotechnology 72, 1136-1143, 2006) wherein a recombinant yeast strain *Saccharomyces cerevisiae* MT8-1 is constructed to ferment the xylose and cellooligosaccharides by integrating genes for the intercellular expressions of xylose reductase and xylitol dehydrogenase from *Pichia stipitis*, and xylulokinase from *Saccharomyces cerevisiae* and a gene for displaying β3-glucosidase from *Aspergillus acleatus* on the cell surface. In the fermentation of the sulfuric acid hydrolysate of wood chips, xylose and cellooligosaccharides are completely fermented after 36 h by the recombinant strain with 41% ethanol yield. The draw backs are the recombinant strain showed fermentation of xylose and oligosaccharides at temperature 32-35° C. requiring high energy input for the cooling the fermentation broth and recovery of ethanol by distillation. The specific productivity on hydrolysate was 0.4-0.42 $g.g^{-1}.h^{-1}$ in the batch process. The recombinant strains have the low stability.

Reference may be made to (Saha and Cotta, Biotechnology Progress, 22, 449-453, 2006) wherein an ethanol yield of 0.46 g/g of available sugars (0.29 g/g straw) using recombinant *Escherichia coli* strain FBR5 from the fermentation of alkaline peroxide pretreated and enzyme saccharified wheat straw hydrolysate is obtained at pH 6.5 and 37° C. in 48 h. The draw backs are the ethanol productivity 0.4 g.l$^{-1}$.h$^{-1}$ is low in batch process as compared to other prior art. The recombinant strains have the low stability.

Reference may be made to (U.S. Pat. No. 5,554,520 dated Oct. 9, 1996) wherein novel plasmids comprising genes which code for the alcohol dehydrogenase and pyruvate decarboxylase have been transformed with genes coding for alcohol dehydrogenase and pyruvate. The recombinant strain E. coli TC4 has been constructed by transforming the alcohol dehydrogenase and pyruvate decarboxylase genes from Z. mobilis. The ethanol yield on glucose, lactose and xylose was 94%, 80% and 100% of theoretical yield respectively. The ethanol productivity is 0.64-1.4 g.l$^{-1}$.h$^{-1}$. The draw backs are the recombinant strain E. coli TC4 could ferment hexose and pentose sugars at 37° C. with low ethanol productivity. The recombinant strains have low stability.

Reference may be made to (U.S. Pat. No. 7,285,403 dated 23 Oct. 2007) wherein xylose-fermenting recombinant yeast strains expressing xylose reductase, xylitol dehydrogenase, and xylulokinase and having reduced expression of PHO13 or a PHO13 ortholog, used for fermenting xylose to obtain ethanol. The recombinant strain of S. cerevisiae is developed, by expressing XYL1 and XYL2 from P. stipitis under the control of the GAPHD (TDH1) promoter, a strong constitutive S. cerevisiae promoter, and engineered to contain multiple copies of XYL3 with its native P. stipitis promoter integrated into the S. cerevisiae genome using a tunable expression vector that allows various expression levels by achieving different integrated copy numbers. The maximum ethanol concentrations are 5.4 g/l and 10.7 g/l for the FPL-YSX3 and the FPL-YSX3P, respectively from 40 g/l of xylose. The draw backs are very low ethanol yield and fermentation occurred at 37° C.

Reference may be made to (Singh et. al; World Journal of Microbiology & Biotechnology 14, 823-834, 1998) wherein application of thermophilic yeast in ethanol production has been reported by using Kluyveromyces marxianus IMB-3 strain MTCC 1288 which showed maximum ethanol yield at 45° C. from various mono and disaccharide sugars. The yeast strain showed 35 gl$^{-1}$ ethanol yields from 100 gl$^{-1}$ sucrose in 13 hr in a batch fermentation process. Further application of yeast Kluyveromyces marxianus IMB-3 in an Indian distillery for industrial scale ethanol production from molasses showed 6-7.2% ethanol concentration in a batch fermentation of 18 hr as compared to Saccharomyces cerevisiae producing same concentration of ethanol in 25 hr. The drawbacks are production of ethanol from sucrose by thermophilic yeast such as Kluyveromyces marxianus IMB-3 strain MTCC 1288 could be achieved maximum at 45° C. with 68% of theoretical yield in batch fermentation. The highest productivity of ethanol from glucose and molasses by immobilized cells of Kluyveromyces marxianus IMB-3 could be achieved was 1.41 gl$^{-1}$h$^{-1}$ and 9.41 gl$^{-1}$h$^{-1}$ with ethanol yield of 90% to 68% of theoretical yield respectively in a continuous fermentation process. However, the drawback of the said process was that the strain was not used for ethanol production from lignocellulosic biomass hydrolysate and the strain showed lower productivity of ethanol on glucose and molasses that limits the scope of lowering of process cost.

Reference may be made to (U.S. Pat. No. 7,344,876 dated 18 Mar. 2008) wherein the yeast strains of the genus Kluyveromyces sp. are disclosed to produce ethanol from lignocellulosic waste materials. The strains have the capability to ferment cellulose, hexoses, pentoses, or hemicelluloses from waste materials to ethanol. The draw backs are the yeast Kluyveromyces sp. produced ethanol at very low yield and temperature 45° C. from lignocellulosics waste material.

Reference may be made to (Shin et. al; International Journal of Systematic and Evolutionary Microbiology, Vol 51, 2167-2170, 2001) wherein a thermophilic yeast strain, Candida thermophilia was isolated from soil of Korea that has maximum growth temperature of 50-51° C., along with certain other physiological characteristics. The drawback is the strain has very low ethanol yield.

Reference may be made to (U.S. Pat. No. 4,094,742) wherein a mixed culture of thermophilic cellulolytic sporocytophaga and thermophilic ethanol-producing Bacillus is admixed with a suspension of cellulose in nutrient mineral broth and the resulting mixture is fermented at a pH ranging from 7 to 8 and at a temperature of 50° C. to 65° C. to produce ethanol. The drawbacks are the mixed culture of fungus and bacteria that does not contain any yeast, could produce 10% ethanol based on cellulose used as substrate which is 40% of theoretical yield and slow rate of production @1.9 gl$^{-1}$h$^{-1}$.

Reference may be made to (Georgieva and Ahring, Applied Microbiology and Biotechnology, 77, 61-68, 2007) wherein the thermophilic anaerobic bacterial strain Thermoanaerobacter BGT1L1 has been used to ferment undetoxifed corn stover hydrolysate in a continuous immobilized reactor system at 70° C. with ethanol yield 0.39-0.42 g/g sugars consumed. Xylose in corn stover hydrolysate is utilized to produce ethanol by the bacteria nearly 89-98%. The draw backs are the sugar uptake and ethanol conc. in continuous process are very low.

Reference may be made to (WO/2007/053600 dated Oct. 5, 2007 and WO/2007/130984 dated 15 Nov. 2007) wherein mutant thermophilic organisms of Thermoanaerobacterium saccharolyticum that consume a variety of biomass derived substrates are disclosed. 30 g/l ethanol was produced in 140 hr when the SSF was performed with 80 g/l avicel. The draw backs are the ethanol productivity (0.214 gl$^{-1}$h$^{-1}$) is very low.

Reference may be made to (U.S. Pat. No. 5,182,199 dated 26 Jan. 1993) wherein the production of ethanol by a process in which a strain of Bacillus stearothermophilus or other thermophilic, facultative anaerobic bacterium at 70° C. is disclosed. The anaerobic fermentation is carried out with continuing removal of ethanol at 70° C. and the fermentative activity of the bacterium is maintained by withdrawing a proportion of the anaerobic fermentation medium on a continuing basis preferably with removal of ethanol and allowing the bacteria therein to multiply aerobically, using residual sugars or metabolites thereof present in the medium, before being returned to the anaerobic fermentation. The ethanol yield 91% of theoretical yield with productivity 0.6 gl$^{-1}$h$^{-1}$ is obtained with 5% w/v sucrose, where 97% sucrose is consumed. The draw backs are the bacteria utilized sucrose as raw material and showed low productivity on ethanol production. Above 4% w/v ethanol concentration ethanol inhibits the fermentation.

Reference may be made to (U.S. Pat. No. 5,580,389 dated Mar. 12, 1996 and U.S. Pat. No. 5,820,687 dated 13 Oct. 1998) wherein an economically viable method for producing sugars using concentrated acid hydrolysis of biomass containing cellulose and hemicellulose is disclosed. This method involves the use of a resin separation unit wherein the sugars are adsorbed on a strong acid resin. The resin separation unit is preferably a cross-linked polystyrene divinylbenzene cation exchange resin bed, wherein the resin is cross linked with divinylbenzene and treated with sulfuric acid to produce a strong acid resin. Preferably, the divinylbenzene is at a concentration of from about 6% to about 8%. The resin bed has a tapped bed density of 0.6 g/ml to 0.9 g/ml and the resin has a strong acid capacity of at least 2 meq/g. The resin used is DOW XFS 43281.01, available from Dow Chemical. At least 98% of the sugars in the hydrolysate are recovered on washing of the bed. Overall recovery of the acid is 97.3% and the recovery of the sugar is 95.5% at 60° C. The drawbacks are the recovery of sugars on washing will dilute the sugar conc. in the hydrolysate.

Reference may be made to (Appua Nestor et. al Society for Biosciences and Bioengineering Japan vol 60. p. 130, 1999) wherein reported is alcohol production by a thermophilic yeast Isolated from Philippine soil. The optimum growth of this yeast was observed at 37-40° C. and at pH 4.0-6.0 in a semi-synthetic medium. The drawbacks are the temperature range for ethanol fermentation is lower as compared to other prior art.

Accordingly, keeping in view the drawbacks of the hitherto known prior art, the inventors of the present invention realized that there exists a dire need to provide a novel strain of yeast that grows on sucrose, glucose, xylose, maltose, galactose, cellobiose in a wide temperature range and which ferments glucose, xylose, sucrose and starch to ethanol at high temperature in the range of 40-55° C. and at pH range of 3.5 to 5.5 showing maximum rate of ethanol production i.e., 13.8 $gl^{-1}h^{-1}$ on glucose in continuous fermentation process.

OBJECTS OF THE INVENTION

The main objective of the present invention is to produce ethanol from lignocellulosic biomass at high temperature which obviates the drawbacks of the hitherto known prior art as detailed above.

Another object of the present invention is to provide a novel process for the production of ethanol using the isolated strain *Kluyveromyces*. IIPE453, MTCC 5314.

Still another object of the present invention is to provide a novel isolated strain of the yeast *Kluyveromyces*. IIPE453, MTCC 5314.

Yet another object of the present invention is to provide fermentation of hexose, pentose sugars and mixture of both to ethanol by the thermophilic yeast at temperature range of 40-55° C. at pH range of 3.5 to 5.5 in batch process.

A further objective of the present invention is to provide recovery of fermentable sugars from lignocellulosic biomass by using ion exchange chromatography adsorbing strong acids on mixture of amberlite IRA 904 as strong anion and bauxite as weak anion as ion exchange resins.

Still another objective of the present invention is to provide recycle of acid obtained from anion exchanger for further hydrolysis of fresh lignocellulosic biomass.

Yet another objective of the present invention is to provide growth of the thermophilic yeast using xylose rich hydrolysate that obtained in first stage sugar cane bagasse hydrolysis at temperature range of 37-55° C. and pH range 3.0 to 6.0.

Still another objective of the present invention is to provide fermentation of glucose and xylose mixture in sugar cane bagasse hydrolysate to ethanol by the thermophilic yeast at temperature range of 40-55° C. at pH range of 3.0 to 5.5 in batch process.

Another objective of the present invention is to provide fermentation of glucose and xylose mixture in sugar cane bagasse hydrolysate to ethanol by the thermophilic yeast at temperature range of 40-65° C. at pH range of 3.5 to 5.5 in continuous process with cell recycle.

Yet another objective of the present invention is to provide in situ ethanol recovery from fermenter by air/gas stripping.

SUMMARY OF THE INVENTION

The present invention relates to thermophilic yeast, *Kluyveromyces* IIPE453, MTCC 5314, an ascomycetous yeast of the fungal family saccharomycetaceae, order endomycetales, isolated by the inventors from soils of Dehradun, India and applied by the inventors in production of ethanol using hexose and pentose individually or in mixture; wherein the novel strain grows on sucrose, glucose, xylose, maltose, galactose, cellobiose in the temperature range of 37-55° C. and ferment glucose, xylose, sucrose and starch to ethanol in the temperature range of 40-55° C. and at pH range of 3.5 to 5.5 showing maximum rate of ethanol production i.e.; 13.8 $g.l^{-1}h^{-1}$ on glucose in continuous fermentation process in comparison to other yeast strains including thermo tolerant yeast *Kluyveromyces marxianus* IMB-3 reported elsewhere as prior art.

This invention relates to ethanol production from lignocellulosic biomass at high temperature, the process comprises of the hydrolysis of lignocellulosic biomass, recovery of fermentable sugars from hydrolysate, fermentation to ethanol by thermophilic yeast, *Kluyveromyces* sp. IIPE453, MTCC 5314, which exhibits growth and sugar fermentation at the temperature range between 37 to 65° C. and in situ recovery of ethanol by air/gas stripping.

The sugar cane bagasse as lignocellulosic biomass has been hydrolyzed to fermentable sugars in two stages. In first stage the sugar cane bagasse is soaked into by 2-8% w/w sulphuric acid. The temperature in the digester is maintained at 80-100° C. temperature for 1-2 hr and agitation is maintained 1000 rpm in which 37-95% xylose of total xylose present in sugar cane bagasse (around 25%) and 2-15% glucose of total glucose present in sugar cane bagasse (around 40%) is obtained. In second stage 18-65% w/w sulphuric acid is added to residual bagasse taken from first stage hydrolysis. The temperature in the digester is maintained at 80-100° C. temperature for 1 hr and agitation is maintained 1000 rpm in which 10-88% glucose and 5-15% xylose is obtained.

Then the sugars are recovered from the hydrolysate by ion exchange chromatography using amberlite IRA 904 and bauxite as anion resins in the ratio of 5:1 to 1:1. At least one column is requires to recover 80% sugars obtained from the first stage hydrolysis and at least three columns are required to recover entire sugars obtained from the first stage hydrolysis. 95-100% sugars are recovered free of acid and 95% acid is recovered which is recycled for further hydrolysis.

The part of xylose rich hydrolysate that obtained in first stage is used to grow the thermophilic yeast, *Kluyveromyces* sp. IIPE453, MTCC 5314 at the temperature range 37 to 55° C. with specific growth rate 0.15-0.18 $h^{-1}$ and yield 0.5-0.54 g cells/g sugar. The remaining part of xylose rich hydrolysate that obtained in first stage and total glucose rich hydrolysate that obtained in second stage are used for fermentation at the temperature range 40 to 65° C. The fermentation process is demonstrated in batch and continuous with cell recycle with ethanol yield 0.2-0.45 g/g sugars, volumetric productivity 0.44-2.3 $gl^{-1}h^{-1}$ and specific productivity 0.118-0.575 grams $g^{-1}h^{-1}$ in sugarcane bagasse hydrolysate.

The thermophilic yeast, *Kluyveromyces* sp. IIPE453, MTCC 5314, an ascomycetous yeast of the fungal family saccharomycetaceae, order endomycetales, isolated by the inventors from soils of Dehradun, India and applied by the inventors in production of ethanol using hexose and pentose individually or in mixture; wherein the novel strain grows on sucrose, glucose, xylose, arabinose, maltose, galactose, cellobiose, raffinose in the temperature range of 37-55° C. and ferment glucose, xylose, mannose, galactose, sucrose, cellobiose and starch to ethanol in the temperature range of 40-65° C. and at pH range of 3.0 to 5.5 showing maximum rate of ethanol production i.e.; 13.8 $gl^{-1}h^{-1}$ on glucose in continuous fermentation process in comparison to other yeast strains including thermotolerant yeast *Kluyveromyces marxianus* IMB-3 reported elsewhere as prior art.

Accordingly, the present invention provides a novel process for the preparation of ethanol by *Kluyveromyces* species IIPE453 MTCC 5314, comprising the steps:

(a) culturing the strain *Kluyveromyces* species IIPE453 MTCC 5314 in salt medium1 (SM1) wherein the said medium comprising 0.15 g/l di-sodium hydrogen ortho-phosphate, 0.15 g/l potassium di-hydrogen ortho-phosphate, 2.0 g/l ammonium sulphate, 1.0 g/l yeast extract and 10 g/l glucose with pH in the range of 5.0 to 6.5 at a temperature in the range of 37° C. to 55° C. for a period of 24 to 30 hours under stirring to obtain cell biomass;

(b) inoculating the cell biomass as obtained in step (a) in fresh salt medium 2 (SM2) wherein the said medium comprises 0.15 g/l di-sodium hydrogen ortho phosphate, 0.15 g/l potassium di-hydrogen ortho phosphate, 1.0 g/l ammonium sulphate, 1.0 g/l yeast extract supplemented with 50 to 100 g/l of a fermentable substrate of the kind such as herein described with pH in the range of 3.5 to 6.5 at a temperature in the range of 40° C. to 55° C. for a period of 24 to 48 hours under stirring to obtain fermentation broth containing ethanol;

(c) optionally immobilizing the cell biomass as obtained in step (a) onto bagasse chips and inoculating the immobilized biomass in fresh salt medium 2 (SM2) wherein the said medium comprises 0.15 g/l di-sodium hydrogen ortho phosphate, 0.15 g/l potassium di-hydrogen ortho phosphate, 1.0 g/l ammonium sulphate, 1.0 g/l yeast extract supplemented with 50 to 100 g/l of a fermentable substrate of the kind such as herein described with pH in the range of 3.5 to 6.5 at a temperature in the range of 40° C. to 55° C. for a period of 40 to 90 hours under stirring to obtain fermentation broth containing ethanol; and (d) separating the ethanol from the fermentation broth.

Further separating the ethanol from the fermentation broth by methods known in the art.

BRIEF DESCRIPTION OF THE ACCOMPANYING DRAWINGS

FIG. 1: shows the growth of thermophilic yeast, *Kluyveromyces* sp. IIPE453, MTCC 5314 on xylose rich stream that obtained in first stage hydrolysis of sugar cane bagasse at 45° C.

FIG. 2: shows the batch fermentation of glucose at 45° C. by thermophilic yeast, *Kluyveromyces* sp. IIPE453, MTCC 5314.

FIG. 3: shows the batch fermentation of xylose at 45° C. by thermophilic yeast, *Kluyveromyces* sp. IIPE453, MTCC 5314.

FIG. 4: shows the batch fermentation on sugar cane bagasse hydrolysate at 50° C. by thermophilic yeast, *Kluyveromyces* sp. IIPE453, MTCC 5314.

FIG. 5: shows the continuous fermentation with cell recycle at 50° C. and air/gas stripping in sugarcane bagasse hydrolysate by thermophilic yeast, *Kluyveromyces* sp. IIPE453, MTCC 5314 and high stability of the cells.

FIG. 6: shows the flow diagram of the process from lignocellulosics biomass to ethanol production.

DETAILED DESCRIPTION OF THE INVENTION

Source and Geographical Origin of Biomaterial

The thermophilic yeast, *Kluyveromyces* sp. IIPE453 MTCC 5314 was isolated from the soil samples, which were collected from the different dumping sites of crushed sugar cane bagasse in Doiwala Sugar Mill, Doiwala, Dehradun, Uttrakhand (India).

Isolation and Screening of Thermophilic Strains

The Yeast extract peptone dextrose medium [YEPD medium] containing in g/l yeast extract=10; peptone=20; glucose=20; pH 5.0 at 45 and 60° C. was used for isolation of the strain. To isolate pure strain, solid medium was used with 2% agar and 1% gelrite as solidifying agent at 45° C. and 60° C. respectively. The thermophilic ethanologens were screened using different sugars like glucose, mannose, galactose, xylose, arabinose, sucrose, cellobiose and lactose. The phenol red broth medium was inoculated with new isolates and incubated at corresponding temperatures for over night. The change in pH due to acid production by the thermophilic ethanologens was indicative as color change from red to yellow by which we could select the potential ethanologenic strains at 45 and 60° C.

Characteristics of the Strain

The thermophilic yeast, *Kluyveromyces* sp. IIPE453, MTCC 5314, is ascomycetous yeast of the fungal family saccharomycetaceae, order endomycetales. The strain is unicellular, large oval in shape, gram +ve and grows by budding, which forms round, small and spherical surface smooth colonies of cream colour on solid YEPD medium containing 2% agar. The growth cycle of the strain is 28 h with 4 h lag phase. The strain was adapted to grow and ferment different sugars with the increase of temperature from 45° C. to 50° C. The strain is applied by the inventors in production of ethanol using hexose and pentose individually or in mixture; wherein the novel strain grows on sucrose, glucose, xylose, galactose, cellobiose, lactose in the temperature of 50° C. and ferments glucose, xylose, sucrose and starch to ethanol in the temperature of 50° C. and at pH 5.5, shown in table 1.

TABLE 1

The growth and ethanol fermentation yield by thermophilic yeast, *Kluyveromyces* sp. IIPE453 MTCC 5314 at 50° C. on different carbon sources

| Sugar Substrate | Biomass yield (% $Y_{X/S}$) | Ethanol concentration %(v/v) | Ethanol yield (% $Y_{P/S}$) |
|---|---|---|---|
| Glucose | 20 | 10.4 | 46 |
| Galactose | 20 | 1.2 | 47 |
| Mannose | 12 | 0.83 | 33 |
| Xylose | 43 | 0.25 | 10 |
| Arabinose | 6 | 0 | 0 |
| Sucrose | 13 | 1.27 | 50 |
| Lactose | 22 | 0.1 | 16.8 |
| Cellobiose | 35 | 0.02 | 4.3 |
| Raffinose | 34 | 0.1 | 11 |

Process Description for Ethanol Production by Thermophilic Yeast

Microorganisms and Culture Conditions

The thermophilic yeast *Kluyveromyces* sp. IIPE453 (MTCC 5314) was grown in salt medium1 (SM1) containing 0.15 g/l di-sodium hydrogen ortho-phosphate, 0.15 g/l potassium di-hydrogen ortho-phosphate, 2.0 g/l ammonium sulphate, 1.0 g/l yeast extract and 10 g/l glucose with pH range 5.0-6.5 at 37-55° C. Fermentation was carried out in salt medium 2 (SM2) prepared in hydrolysate containing 0.15 g/l di-sodium hydrogen ortho phosphate, 0.15 g/l potassium di-hydrogen ortho phosphate, 1.0 g/l ammonium sulphate, 1.0 g/l yeast extract with pH range 3.5-6.5 at 40 to 55° C.

This invention relates to ethanol production from lignocellulosic biomass at high temperature, the process comprises of the hydrolysis of lignocellulosic biomass, recovery of fermentable sugars from hydrolysate, fermentation to ethanol by thermophilic yeast, *Kluyveromyces* sp. IIPE453, MTCC 5314, which exhibits growth and sugar fermentation at the temperature range between 37 to 65° C. and in situ recovery of ethanol by air/gas stripping.

Saccharification of Lignocellulosic Biomass

Acid Hydrolysis

The sugarcane bagasse as lignocellulosic biomass has been hydrolyzed to fermentable sugars in two stages. In first stage the sugar cane bagasse is soaked into by 2-10% w/w sulphuric acid with solid to liquid ratio 1:10 to 1:4.2. The temperature in the digester is maintained at 80-100° C. temperature for 1-2 hr and agitation is maintained 1000 rpm. The slurry is cool down and then filtered to separate out liquid from the solid. The residual bagasse is washed with 2-4 L water and again filtered. The sugars and furfural concentrations are estimated. 37-95% xylose of total xylose present in sugar cane bagasse (around 25%), 2-15% glucose of total glucose present in sugar cane bagasse (around 40%) and 120-950 mg/l furfural are obtained. The best result is obtained at 8% w/w sulphuric acid with solid to liquid ratio 1:6 in 1.5 hr where maximum xylose is obtained with low concentration of furfural.

In second stage 18-65% w/w sulphuric acid is added to residual bagasse taken from first stage hydrolysis. The temperature in the digester is maintained at 80-110° C. temperature for ½ hr and agitation is maintained 1000 rpm. The water was added to dilute the acid up to 18-20% w/w and again the temperature in the digester is maintained at 80-100° C. temperature for ½ hr and agitation is maintained 1000 rpm. The slurry is cool down and then filtered to separate out liquid from the solid. The residual bagasse is washed with 2-4 L water and again filtered. The sugars and furfural concentrations are estimated. 10-88% glucose and 5-15% xylose is obtained.

Recovery of Sugars from Hydrolysate

The sugars are recovered from the bagasse hydrolysate by ion exchange chromatography using amberlite IRA 904 and bauxite as anion resins. A glass column having 100 cm length and 3 cm diameter is packed with amberlite IRA 904 and bauxite mixture in the ratio of 5:1 to 1:1. The bagasse hydrolysate containing 35-80 g/l sugar conc. and 60-200 g/l sulphuric acid conc. is passed through the column with flow rate 4-17 ml/min. The sulphuric acid is retained in the column and sugars are passed through the column. The acid free sugars are collected. As acid starts coming with sugars the flow is stopped and the column requires regenerating. During the regeneration with water first sugars come out with acid and then acid comes out. The sugars containing mild acid are again passed through the column. At least one column is requires to recover 80% sugars obtained from the first stage hydrolysis and at least three columns are required to recover entire sugars obtained from the second stage hydrolysis. 95-100% sugars are recovered free of acid and 95% acid is recovered which is recycled for further hydrolysis of new sugarcane bagasse.

Growth of Microorganism and Ethanol Fermentation on Sugarcane Bagasse Hydrolysate The present invention provides a novel process for the preparation of ethanol by *Kluyveromyces* species IIPE453 MTCC 5314, comprising the steps:

(a) culturing the strain *Kluyveromyces* species IIPE453 MTCC 5314 in salt medium1 (SM1) wherein the said medium comprising 0.15 g/l di-sodium hydrogen ortho-phosphate, 0.15 g/l potassium di-hydrogen ortho-phosphate, 2.0 g/l ammonium sulphate, 1.0 g/l yeast extract and 10 g/l glucose with pH in the range of 5.0 to 6.5 at a temperature in the range of 37° C. to 55° C. for a period of 24 to 30 hours under stirring to obtain cell biomass;

(b) inoculating the cell biomass as obtained in step [a] in fresh salt medium 2 (SM2) wherein the said medium comprises 0.15 g/l di-sodium hydrogen ortho phosphate, 0.15 g/l potassium di-hydrogen ortho phosphate, 1.0 g/l ammonium sulphate, 1.0 g/l yeast extract supplemented with 50 to 100 g/l of a fermentable substrate of the kind such as herein described with pH in the range of 3.5 to 6.5 at a temperature in the range of 40° C. to 55° C. for a period of 24 to 48 hours under stirring to obtain fermentation broth containing ethanol;

(c) optionally immobilizing the cell biomass as obtained in step (a) onto bagasse chips and inoculating the immobilized biomass in fresh salt medium 2 (SM2) wherein the said medium comprises 0.15 g/l di-sodium hydrogen ortho phosphate, 0.15 g/l potassium di-hydrogen ortho phosphate, 1.0 g/l ammonium sulphate, 1.0 g/l yeast extract supplemented with 50 to 100 g/l of a fermentable substrate of the kind such as herein described with pH in the range of 3.5 to 6.5 at a temperature in the range of 40° C. to 55° C. for a period of 40 to 90 hours under stirring to obtain fermentation broth containing ethanol;

(d) separating the ethanol from the fermentation broth.

The fermentable substrates of the present invention are those compounds, materials and substances which convert to ethanol by the process of Ethanol Fermentation.

Further the ethanol may be separated from the fermentation broth by utilizing different methods known in the art. The ethanol may be separated by distillation, filtration through membranes of definite pore size, or through sorbet systems known in the art.

A publication entitled "Recovery of ethanol from fermentation broths using selective sorption-desorption," Pitt W W Jr, Haag G L, Lee D D, Biotechnology Bioengineering. 1983 January; 25(1):123-31 discloses a process wherein sorbent systems have been utilized for separation of ethanol from fermentation broth.

Further pre-evaporation techniques may be utilized, pre-evaporation is an energy efficient method which combines membrane permeation and evaporation.

Ethanol may also be separated by filtration using different membranes and membrane systems known in the art. One such membrane system has been disclosed in the publication entitled "Selective ethanol extraction from fermentation broth using a silicalite membrane"; Mikihiro Nomura, tang Bin, Sin-ichi Nakao Separation and Purification Technology Volume 27, Issue 1, 1 Apr. 2002, pages 59-66. The methods of separation are not restricted to as disclosed above.

Ethanol can be extracted from the fermentation broth by any method known in the art.

The process of present invention is carried out in two steps as follows:

a. Growth of the thermophilic yeast, *Kluyveromyces* sp. IIPE453, MTCC 5314

The thermophilic yeast, *Kluyveromyces* sp. IIPE453, MTCC 5314 5487, an ascomycetous yeast of the fungal family saccharomycetaceae, order endomycetales, isolated by the inventors from soils of Dehradun, India and applied by the inventors in production of ethanol using hexose and pentose individually or in mixture; wherein the novel strain grows on sucrose, glucose, xylose, arabinose, maltose, galactose, cellobiose, raffinose in the temperature range of 37-55° C. The strain is grown in salt medium hereafter would be known as SM1 medium, containing 0.15 g/l di-sodium hydrogen ortho-phosphate, 0.15 g/l potassium di-hydrogen ortho-phosphate, 2.0 g/l ammonium sulphate, 1.0 g/l yeast extract and 10 g/l carbon source as one of sucrose, glucose, xylose, arabinose, maltose, galactose, cellobiose, raffinose at pH 5.0. The strain of present invention exhibits a specific growth rate of 0.35 h$^{-1}$ to 0.55 hr$^{-1}$ and the yield coefficient of 0.31 to 0.52 g cells/g glucose at 45° C. to 55° C. which are higher to other fermenting yeast strains.

The strain is also grown on bagasse hydrolysate. The part of xylose rich hydrolysate that obtained in first stage hydrolysis is used to grow the thermophilic yeast, $Kluyveromyces$ sp. IIPE453, MTCC 5314, at the temperature range 37 to 55° C. with specific growth rate 0.15-0.18 h$^{-1}$ and yield 0.5-0.54 g cells/g sugar.

b. Ethanol fermentation by thermophilic yeast, $Kluyveromyces$ sp. IIPE453, MTCC 5314

The thermophilic yeast, $Kluyveromyces$ sp. IIPE453, MTCC 5314 is able to ferment glucose, xylose, mannose, galactose, sucrose, cellobiose and starch to ethanol in the temperature range of 40-65° C. and at pH range of 3.0 to 5.5 showing maximum rate of ethanol production i.e.; 13.8 gl$^{-1}$h$^{-1}$ on glucose in continuous fermentation process in comparison to other yeast strains including thermotolerant yeast $Kluyveromyces$ $marxianus$ IMB-3 reported elsewhere as prior art.

Fermentation is carried out in medium prepared with the composition of 0.15 g/l di-sodium hydrogen ortho phosphate, 0.15 g/l potassium di-hydrogen ortho phosphate, 1.0 g/l ammonium sulphate, 1.0 g/l yeast extract with pH 5.0 hereafter would be known as SM2 medium.

The remaining part of xylose rich hydrolysate that obtained in first stage and total glucose rich hydrolysate that obtained in second stage hydrolysis are used for fermentation at the temperature range 40 to 65° C. The fermentation process is demonstrated in batch and continuous with cell recycle with ethanol yield 0.2-0.45 g/g sugars in hydrolysate, volumetric productivity 0.44-2.3 gl$^{-1}$h$^{-1}$ and specific productivity 0.118-0.575 gram g$^{-1}$h$^{-1}$ in sugarcane bagasse hydrolysate.

In batch fermentation process the conc. of thermophilic yeast, $Kluyveromyces$ sp. IIPE453, MTCC 5314 5487, is kept around 10% of initial fermentable sugars in the hydrolysate. The temperature and pH are controlled throughout the fermentation. The agitation is maintained at 250 rpm. The air/N$_2$ gas is passed through the fermenter for stripping the ethanol for in situ recovery. The exhaust gases are passed through the condenser and the ethanol from the exhaust gases is collected.

In the continuous process with cell recycle the feed containing bagasse hydrolysate is provided continuously to the fermenter and the outlet stream is pumped to cell separator where the cells are separated by the gravitational settling. The lower layer containing cells rich broth and residual sugar is pumped to fermenter and upper layer containing low cell conc. broth is pumped out. The air/N$_2$ gas is passed through fermenter continuously for stripping the ethanol for in situ recovery. The exhaust gases are passed through the condenser and the ethanol from the exhaust gases is collected.

In an embodiment of the present invention the yeast strain $Kluyveromyces$ sp. IIPE453, MTCC 5314, showed that the growth phase started after 4 hr and reaches to stationary phase within 20 hr at the specific growth rate of 0.15 h$^{-1}$ and the yield coefficient of 0.51 g cells/g sugars present in xylose rich stream of bagasse hydrolysate at 45° C. The data indicates that the specific growth rate and yield coefficient of the strain IIPE453 are higher to other fermenting yeast as $S.$ $cerevisiae$ and $Kluyveromyces$ $marxianus$ IMB3 at 45° C.

In another embodiment of the present invention, the gram positive yeast strain $Kluyveromyces$ IIPE453 MTCC 5314 grows with budding on different hexose sugars such as sucrose, glucose, maltose, galactose, cellobiose and pentose sugar such as xylose and ferment hexose sugars such as glucose, sucrose, starch and pentose sugar such as xylose to ethanol.

In another embodiment of the present invention the yeast strain $Kluyveromyces$ sp. IIPE453 MTCC 5314, ferment bagasse hydrolysate containing a mixture of glucose and xylose to ethanol in the temperature range 45-65° C. and pH 5.0 with ethanol yield of 39-82.2% of theoretical yield, volumetric productivity of 0.74-2.3 gl$^{-1}$h$^{-1}$ and specific productivity 0.118-0.575 g ethanol/g cellsh$^{-1}$.

In another embodiment of the present invention yeast strain $Kluyveromyces$ IIPE453 MTCC 5314 ferment starch containing a mixture of glucose and maltose to ethanol at 45° C. and pH 4.5 with ethanol yield of 58% of theoretical yield and productivity of 0.125 gl$^{-1}$h$^{-1}$. In a further embodiment of the present invention the strain $Kluyveromyces$ sp. IIPE453, MTCC 5314, also grows on sucrose, glucose, xylose, maltose, galactose, cellobiose and ferment glucose, sucrose, xylose, starch to ethanol in the temperature range of 40-65° C. and at pH range of 3.5 to 5.5 in batch and continuous fermentation process and showing maximum rate of ethanol production 13.8 gl$^{-1}$h$^{-1}$ on sugarcane bagasse at 45° C. in continuous fermentation process.

In another embodiment of the present invention the yeast strain $Kluyveromyces$ sp. IIPE453 MTCC 5314, shows the high stability 20 days in the continuous process with cell recycle 50° C. in sugarcane bagasse hydrolysate.

In another embodiment of the present invention the yeast strain $Kluyveromyces$ sp. IIPE453, MTCC 5314, can utilize glucose and xylose simultaneously for growth and fermentation.

In another embodiment of the present invention the continuous processes for the production of ethanol was developed with the immobilized cells of the strain $Kluyveromyces$ sp. IIPE453, MTCC 5314, on bagasse chips with 30 ml/h to 60 ml/h flow rates and initial glucose concentrations 50 g/l to 100 g/l were performed at 40 to 50° C. and observed the productivity in the range of 0.78 to 13.8 gl$^{-1}$h$^{-1}$ and highest productivity of 13.8 gl$^{-1}$h$^{-1}$ on dilution rate 0.3 to 0.82 h$^{-1}$.

In another embodiment of the present invention yeast strain $Kluyveromyces$ sp. IIPE453, MTCC 5314, ferment starch containing a mixture of glucose and maltose to ethanol at 45° C. and pH 4.5 with ethanol yield of 58% of theoretical yield and productivity of 0.125 gl$^{-1}$h$^{-1}$. In another embodiment of the present invention the process provides the recovery of fermentable sugars from the sugarcane hydrolysate by ion exchange chromatography using amberlite IRA 904 and bauxite mixture.

In another embodiment of the present invention the process provides the recycling of sulphuric acid for the fresh hydrolysis of sugarcane bagasse.

In another embodiment of the present invention the process provides the in situ recovery of ethanol by air/N$_2$ stripping at high temperature.

In an embodiment of the present invention, the strain of present invention is gram positive and grows on sucrose, glucose, xylose, maltose, galactose, cellobiose and ferments glucose, sucrose, xylose, starch to ethanol as individual substrate or in a mixture that obtained from hydrolysis of sugarcane bagasse or cassava starch in the temperature range of 40-65° C. and at pH range of 3.5 to 5.5 in batch and continuous fermentation process.

In another embodiment of the present invention the strain of present invention exhibits a specific growth rate of 0.35 h$^{-1}$ to 0.55 hr$^{-1}$ and the yield coefficient of 0.31 to 0.52 g cells/g glucose at 45° C. to 55° C. which are higher than other fermenting yeast strain.

The strain of present invention exhibits high stability in long term under continuous fermentation at high temperature of 40-65° C.

The strain of present invention can sustain high ethanol tolerance up to 10.34% v/v without inhibition at 45° C.

In another embodiment of present invention the strain of present invention produces ethanol continuously preferably for more than 100 hrs as immobilized cells on bagasse chips on glucose and sucrose 30 to 60 ml/hr flow rates and initial concentrations 50 to 100 g/l were performed at 40 to 50° C. with the productivity of 0.78 to 13.8 $gl^{-1}h^{-1}$ on dilution rate 0.3 to 0.82 $hr^{-1}$.

In another embodiment of the present invention the strain of present invention grows on sugarcane bagasse hydrolysate with the specific growth rate of 0.15 $h^{-1}$ to 0.18 $h^{-1}$ and the yield coefficient of 0.50 to 0.54 g cells/g glucose at 45 to 55° C. which are higher to other fermenting yeast strain the temperature of 45° C.

In an embodiment in the process as stated above the fermentable substrate is selected from monosaccharide and disaccharide sugars, bagasse, hydrolysate of lignocellulosic biomass or starch based biomass either singly or in any combination.

In a further embodiment of the present invention in the process stated above the sugars are preferably glucose, maltose, xylose, sucrose and starch.

In an embodiment of the invention in the process as stated above the concentration of fermentable sugar in the medium SM2 is preferably 100 g/l.

In an embodiment of the invention in the process as stated above the temperature of fermentation in step [b] is preferably 50 degree C.

In an embodiment of the invention in the process as stated above the pH in step [b] is preferably 5.5.

In an embodiment of the invention in the process as stated above the productivity of ethanol is as high as 13.8 grams per liter per hour.

In an embodiment of the invention in the process as stated above the yield of ethanol is as high as 58.75%.

In an embodiment of the invention in the process as stated above provides 98-100% acid free sugar recovery from sugarcane bagasse hydrolysate.

In an embodiment of the invention in the process as stated above provides recycling of 80-95% sulphuric acid obtained in regeneration of ion exchange column for further hydrolysis of fresh sugarcane bagasse.

EXAMPLES

The following examples are given by way of illustration and therefore should not be construed to limit the scope of the present invention in any way.

Growth of the Strain

Example-1

The strain *Kluyveromyces* IIPE453 MTCC 5314 was grown in salt medium hereinafter referred to as SM 1 medium, containing 0.15 g/l di-sodium hydrogen ortho phosphate, 0.15 g/l potassium di-hydrogen ortho-phosphate, 2.0 g/l ammonium sulphate, 1.0 g/l yeast extract and 10 g/l glucose at pH 5.0. Growth of the yeast strain was carried out in a 250 ml conical flask containing 50 ml of the SM1 medium inoculated with a loop full of preserved frozen yeast culture and incubated in environmental shaker (Infoss, Switzerland) at 45° C. and 180 rpm. 1 ml culture sample was withdrawn at 2 h interval and dry weight of the yeast cells and glucose concentration was determined. The dry cell mass was analyzed by centrifuging in eppendorf tube by using Eppendorf Centrifuge 5415 C at 10,000 rpm for 5 min, washing twice with distilled water and drying in vacuum oven at 70° C. and 50 mm vacuum to a constant weight. The specific growth rate of the yeast *Kluyveromyces* sp. IIPE453 (MTCC 5314) on glucose was determined as 0.55 h-1. The yield coefficient of the strain was 0.22.

Example-2

Growth of the yeast strain was carried out in a 250 ml conical flask containing 50 ml of the SM1 medium inoculated with a loop full of preserved frozen yeast culture and incubated in environmental shaker (Infoss, Switzerland) at 60° C. and 180 rpm. 1 ml culture sample was withdrawn at 2 hr interval and dry weight of the yeast cells and glucose concentration was determined. The dry cell mass was analyzed by centrifuging in eppendorf tube by using Eppendorf Centrifuge 5415 C at 10,000 rpm for 5 min, washing twice with distilled water and drying in vacuum oven at 70° C. and 50 mm vacuum to a constant weight. The specific growth rate of the yeast *Kluyveromyces* sp. IIPE453 (MTCC 5314) on glucose was determined as 0.02 $h^{-1}$. The yield coefficient of the strain was 0.01.

Example-3

Growth of the yeast strain was carried out in a 250 ml conical flask containing 50 ml of the SM1 medium replacing glucose with sucrose at 10 g/l, inoculated with a loop full of preserved frozen yeast culture and incubated in environmental shaker (Infoss, Switzerland) at 50° C. and 180 rpm. 1 ml culture sample was withdrawn at 2 hr interval and dry weight of the yeast cells and glucose concentration was determined. The dry cell mass was analyzed by centrifuging in eppendorf tube by using Eppendorf Centrifuge 5415 C at 10,000 rpm for 5 min, washing twice with distilled water and drying in vacuum oven at 70° C. and 50 mm vacuum to a constant weight. The specific growth rate of the yeast *Kluyveromyces* sp. IIPE453 (MTCC 5314) on sucrose was determined as 0.7 $h^{-1}$. The yield coefficient of the strain on sucrose was determined as 0.38.

Example-4

Growth of the yeast strain was carried out in 3 different 250 ml conical flasks each containing 50 ml of the SM1 medium replacing glucose with xylose, cellobiose and galactose, wherein the concentration of the sugars is 10 g/l separately in each flask. These flasks were separately inoculated with a loop full of preserved frozen yeast culture and incubated in environmental shaker (Infoss, Switzerland) at 45° C. and 180 rpm. 1 ml culture sample was withdrawn at 2 hr interval and dry weight of the yeast cells and glucose concentration was determined. The dry cell mass was analyzed by centrifuging in eppendorf tube by using Eppendorf Centrifuge 5415 C at 10,000 rpm for 5 min, washing twice with distilled water and drying in vacuum oven at 70° C. and 50 mm vacuum to a constant weight. Total reducing sugars was determined by DNS reagent measuring optical density in a Double Beam UV-VIS Spectrophotometer, Chemito 2600 at 575 nm. Xylose was determined by p-bromo aniline reagent at 520 nm. The yield coefficient of the strain of the yeast *Kluyveromyces* sp. IIPE453 (MTCC 5314) on xylose, cellobiose and galactose was determined as 0.43, 0.35 and 0.20 respectively.

Example-5

Growth of the yeast strain was carried out in 4 different 250 ml conical flasks each containing 50 ml of the SM1 medium replacing glucose with xylose and cellobiose, maltose and galactose @10 g/l separately in each flask. Each of the said flasks was inoculated with a loop full of preserved frozen yeast culture and incubated in environmental shaker (Infoss, Switzerland) at 45° C. and 180 rpm. 1 ml culture sample was withdrawn at 2 hr interval and dry weight of the yeast cells and glucose concentration was determined. The dry cell mass was analyzed by centrifuging in eppendorf tube by using Eppendorf Centrifuge 5415 C at 10,000 rpm for 5 min, washing twice with distilled water and drying in vacuum oven at 70° C. and 50 mm vacuum to a constant weight. Total reducing sugars was determined by DNS reagent measuring optical density in a Double Beam UV-VIS Spectrophotometer, Chemito 2600 at 575 nm and xylose was determined by p-bromo aniline reagent at 520 nm. The yield coefficient of the strain of the yeast *Kluyveromyces* sp. IIPE453 (MTCC 5314) on xylose, maltose, cellobiose and galactose was determined as 0.48, 0.34, 0.30 and 0.31 respectively.

Example-6

Growth of the yeast strain was carried out in a 5 litre fermenter of Bioflow-110 containing 5 litre of the SM1 medium in xylose rich hydrolysate with xylose conc. 15 g/l, inoculated with yeast culture grown in 200 ml SM1 medium in xylose rich hydrolysate. The temperature, pH and DO were controlled at 45° C., 5.5 and 40% respectively. The DO was controlled by the agitation and the air flow rate was 0.6 VVM. 2 ml culture sample was withdrawn at 2 hr interval and dry weight of the yeast cells and sugar concentration was determined, shown in FIG. 1. The dry cell mass will be analyzed by centrifuging in eppendorf tube by using Eppendorf Centrifuge 5415 C at 10,000 rpm for 5 min, washing twice with distilled water and drying in vacuum oven at 70° C. and 50 mm vacuum to a constant weight. The specific growth rate of the yeast *Kluyveromyces* sp. IIPE453 (MTCC 5314) on xylose rich hydrolysate was determined as 0.154 $h^{-1}$. The yield coefficient of the strain on hydrolysate was determined as 0.51.

Hydrolysis of Bagasse by Sulphuric Acid Treatment

Example-7

Sugar cane bagasse, collected from sugar industry was hydrolyzed by acid treatment in two stages. The first stage hydrolysis was performed in 30 L reactor with 1 kg dry bagasse. 7.58% w/w sulphuric acid was added at 1:6 solid-liquid ratio. The temperature and agitation were maintained 95° C. and 1000 rpm respectively for 1.5 h. The samples were taken at 15 min intervals and estimated sugars and furfural conc. The total xylose and glucose on dry bagasse basis were recovered 27.5% w/w and 2.5% w/w respectively.

The second hydrolysis was performed in 30 L reactor with the residual bagasse from first hydrolysis. 70% w/w sulphuric acid was added. The temperature was maintained 80° C. for ½ h. Then 2 L water was added to make the acid conc. 18.7% w/w and temperature was maintained at 95° C. for 1 h. The total glucose on dry bagasse basis was recovered 30% w/w.

Sugar Recovery from Bagasse Hydrolysate by Ion Exchange Chromatography

Example-8

The acid from the hydrolysate was recovered by ion exchange chromatography by using amberlite IRA-904 and alumina in 5:1 ratio as ion exchange resin in a glass column having 1 meter length and 3 cm diameter. 44% sugars were recovered with out acid and the remaining sugar with acid was further passed through the column. 75% acid was obtained from the regeneration of the column, which was recycled for the further hydrolysis. The experiment was carried out at room temperature.

Example-9

The acid from the hydrolysate was recovered by ion exchange chromatography by using amberlite IRA-904 and alumina in 5:2 ratio as ion exchange resin in a glass column having 1 meter length and 3 cm diameter. 65% sugars were recovered with out acid and the remaining sugar with acid was further passed through the column. 85% acid was obtained from the regeneration of the column, which was recycled for the further hydrolysis. The experiment was carried out at room temperature.

Ethanol Fermentation Conditions

Example-10

Fermentation was carried out in salt medium 2 [SM2] prepared with the composition of 0.15 g/l di-sodium hydrogen ortho phosphate, 0.15 g/l potassium di-hydrogen ortho phosphate, 1.0 g/l ammonium sulphate, 1.0 g/l yeast extract with pH 6.0 hereinafter known as SM2 medium. Batch fermentation was performed in 1 litre flat bottom jacketed flask was fitted with condenser for arresting of ethanol vapor and inlet for addition of glucose solution. Fermentation carried out with 500 ml of SM2 medium supplemented with glucose making initial concentration of 200 g/l and adding previously grown free cells of *Kluyveromyces* sp. IIPE453 (MTCC 5314) providing initial cell concentration of 5.5 g/l in batch mode for 48 hr. The temperature was maintained at 45° C. and stirred by magnetic stirrer at 50 rpm. 10 ml of fermentation broth was withdrawn at regular interval of 6 hr and analyzed for determination of residual sugar and ethanol concentration in the broth. Total reducing sugars was determined by DNS reagent measuring optical density in a Double Beam UV-VIS Spectrophotometer, Chemito 2600 at 575 nm. The concentration of sugars in the sample was determined from the standard plot of known concentration of the sugar solution versus optical density. Ethanol conc. was determined by calorimetric method by using chromic acid and taking absorbance by Double Beam UV-VIS Spectrophotometer Chemito 2600 at 584 nm. Confirmatory test of presence of ethanol in fermented broth was analyzed by GC using a Chemito 8600 Refinery Gas Analyser with a 4 m long and ⅛ in diameter polar column with Chemosorb 80/60, FID detector using Nitrogen as carrier gas flowing at a rate of 3 ml per minute. Maximum yield of ethanol on glucose, obtained in the batch fermentation process, was 82.34 g/l by the thermophilic strain *Kluyveromyces* sp. IIPE453 achieving 90% of the theoretical yield (51.11%), shown in FIG. 2. Ethanol productivity in the batch fermentation was 1.14 $gl^{-1}h^{-1}$ by *Kluyveromyces* sp. IIPE453 at 45° C. in 72 h as compared to *Kluyveromyces marxianus* IMB-3 having productivity of 0.67 $gl^{-1}h^{-1}$ at 45° C. and *Saccharomyces cereviciae* having productivity of 0.78 $gl^{-1}h^{-1}$ at 35° C. The strain exhibited high ethanol tolerance of 10.34% v/v at 45° C.

Example-11

Example 10 was repeated at 50° C. and ethanol yield of 90% of theoretical yield was obtained in 24 hr showing the productivity of 0.94 $gl^{-1}h^{-1}$.

Example-12

Example 10 was repeated at 45° C. replacing glucose with sucrose with initial concentration of 20 g/l and ethanol yield of 98% of theoretical yield was obtained in 24 hr showing the productivity of 0.81 gl$^{-1}$h$^{-1}$.

Example-13

Example 10 was repeated at 45° C. replacing glucose with xylose with initial concentration of 20 g/l and ethanol yield of 20% of theoretical yield was obtained in 64 hr showing the productivity of 0.027 gl$^{-1}$h$^{-1}$, as shown in FIG. 3.

Example-14

Batch fermentation was performed in 2 litre fermenter of Bioflow-110, which was fitted with condenser for arresting of ethanol vapor and using of bagasse hydrolyzed solution containing glucose and xylose sugars. Fermentation carried out with 2 litre of hydrolysate solution supplemented with inorganic salts and adding previously grown free cells of *Kluyveromyces* sp. IIPE453 (MTCC 5314) in xylose rich hydrolysate providing initial cell concentration of 10 g/l in batch mode for 20 hr. The temperature, pH and agitation were controlled at 50° C., 5.0 and 250 rpm respectively. 10 ml of fermentation broth was withdrawn at regular interval of 2 hr and analyzed for determination of residual sugar, ethanol concentration and dry cell mass in the broth similarly as mentioned in example 9, shown in FIG. 4. Overall yield of ethanol based on consumption of total fermentable sugars present in bagasse hydrolysate was 74% of theoretical yield in the batch fermentation process in 20 hr by the thermophilic strain *Kluyveromyces* sp. IIPE453 (MTCC 5314) achieving a productivity of 0.61 gl$^{-1}$h$^{-1}$.

Example-15

Continuous fermentation was performed in 2 litre fermenter of Bioflow-110 which was fitted with condenser for arresting of ethanol vapor and using of bagasse hydrolyzed solution containing glucose and xylose sugars. Fermentation carried out with 2 litre of hydrolysate solution supplemented with inorganic salts and adding previously grown free cells of *Kluyveromyces* sp. IIPE453 (MTCC 5314) in xylose rich hydrolysate. At steady state the cell concentration was 4 g/l with dilution rate 0.1 h$^{-1}$ and 60% cell recycle. The temperature, pH and agitation were controlled at 45° C., 5.0 and 250 rpm respectively. 35 ml of sample were withdrawn from fermenter stream, recycle stream and product stream at regular interval of 2 hr and analyzed for determination of residual sugar, ethanol concentration and dry cell mass in the each stream similarly as mentioned in example 9. The overall yield of ethanol based on consumption of total fermentable sugars present in bagasse hydrolysate was 82.2% of theoretical yield in the continuous fermentation process by the thermophilic strain *Kluyveromyces* sp. IIPE453 (MTCC 5314) achieving a volumetric productivity of 2.3 gl$^{-1}$h$^{-1}$ and specific productivity 0.575 gg$^{-1}$h$^{-1}$.

Example-16

Example 15 was repeated at 50° C. with dilution rate 0.1 h$^{-1}$. The air was passed through the fermenter for the ethanol stripping. At steady state ethanol concentration in condensate was 33.3 g/l. The overall yield of ethanol based on consumption of total fermentable sugars present in bagasse hydrolysate was 68% of theoretical yield in the continuous fermentation process by the thermophilic strain *Kluyveromyces* sp. IIPE453 (MTCC 5314) achieving a volumetric productivity of 1.86 gl$^{-1}$h$^{-1}$ and specific productivity 0.465 gg$^{-1}$h$^{-1}$.

Example-17

Example 15 was repeated at 50° C. with dilution rate 0.075 h$^{-1}$. The air was passed through the fermenter for the ethanol stripping. At steady state ethanol concentration in condensate was 38 g/l. The overall yield of ethanol based on consumption of total fermentable sugars present in bagasse hydrolysate was 65% of theoretical yield in the continuous fermentation process by the thermophilic strain *Kluyveromyces* sp. IIPE453 (MTCC 5314) achieving a volumetric productivity of 1.25 gl$^{-1}$h$^{-1}$ and specific productivity 0.32 gg$^{-1}$h$^{-1}$.

Example-18

Example 15 was repeated at 50° C. and dilution rate 0.075 h$^{-1}$ by increasing dry cell mass concentration. At steady state ethanol concentration in condensate was 50 g/l. The overall yield of ethanol based on consumption of total fermentable sugars present in bagasse hydrolysate was 70% of theoretical yield in the continuous fermentation process by the thermophilic strain *Kluyveromyces* sp. IIPE453 (MTCC 5314) achieving a volumetric productivity of 1.73 gl$^{-1}$h$^{-1}$ and specific productivity 0.216 gg$^{-1}$h$^{-1}$.

Example-19

Example 15 was repeated at 50° C. and dilution rate 0.075 h$^{-1}$ by changing gas stripping by nitrogen instead of air. At steady state ethanol concentration in condensate was 56.5 g/l. The overall yield of ethanol based on consumption of total fermentable sugars present in bagasse hydrolysate was 70% of theoretical yield in the continuous fermentation process by the thermophilic strain *Kluyveromyces* sp. IIPE453 (MTCC 5314) achieving a volumetric productivity of 1.7 gl$^{-1}$h$^{-1}$ and specific productivity 0.281 gg$^{-1}$h$^{-1}$.

Example-20

Example 15 was repeated at 50° C. and dilution rate 0.075 h$^{-1}$ by adding ferric chloride in feed and no stripping was performed. At steady state ethanol conc. in condensate was 58 g/l. The overall yield of ethanol based on consumption of total fermentable sugars present in bagasse hydrolysate was 74.4% of theoretical yield in the continuous fermentation process by the thermophilic strain *Kluyveromyces* sp. IIPE453 (MTCC 5314) achieving a volumetric productivity of 1.76 gl$^{-1}$h$^{-1}$ and specific productivity 0.266 gg$^{-1}$h$^{-1}$. The strain showed the high stability 20 days in continuous fermentation at 50° C., shown in FIG. 6.

Example-21

Example 16 was repeated at dilution rate 0.075 h$^{-1}$ by changing the temperature 55° C. The overall yield of ethanol based on consumption of total fermentable sugars present in bagasse hydrolysate was 49% of theoretical yield in the continuous fermentation process by the thermophilic strain *Kluyveromyces* sp. IIPE453 (MTCC 5314) achieving a volumetric productivity of 0.99 gl$^{-1}$h$^{-1}$ and specific productivity 0.217 gg$^{-1}$h$^{-1}$.

Example-22

Example 16 was repeated at dilution rate 0.075 h$^{-1}$ by changing the temperature 60° C. The overall yield of ethanol based on consumption of total fermentable sugars present in bagasse hydrolysate was 39% of theoretical yield in the continuous fermentation process by the thermophilic strain *Kluyveromyces* sp. IIPE453 (MTCC 5314) achieving a volumetric productivity of 0.74 gl$^{-1}$h$^{-1}$ and specific productivity 0.118 gg$^{-1}$h$^{-1}$.

Example-23

5 g of Active cells of the yeast strain *Kluyveromyces* sp. IIPE453 (MTCC 5314) was immobilized on 25 g of bagasse chips of size ranging from 5 mm to 8 mm long and soaked into 250 ml SM1 medium with 5 g/l glucose conc. in a 500 ml flak and incubated in a rotary shaker (Infoss, Switzerland) at 45° C. for 30 hr. 10 g immobilized bagasse chips loaded with 130 mg of yeast cells was packed in a column 50 cm long and 2.5 cm i.d. The packing height was 32 cm. The volume of packing was 162 cm$^3$ and void volume was 55 cm$^3$. The fermentation medium SM2 with initial glucose conc. 50 g/l was passed through the column at flow rate 30 ml/hr, dilution rate 0.71 h$^{-1}$ axial velocity 21.3 cm/h respectively. The residence time of the sugar solution was 1.5 hr. The temperature of the column was maintained at 50° C. The highest ethanol 16.8 g/l was produced with productivity 13.8 gl$^{-1}$h$^{-1}$ at dilution rate 0.82 h$^{-1}$.

Example-24

Batch fermentation was performed in 1 litre flat bottom jacketed flask was fitted with condenser for arresting of ethanol vapor and using 5% soluble starch solution. Fermentation was carried out with 500 ml starch solution supplemented with inorganic salts and adding previously grown free cells of *Kluyveromyces* sp. IIPE453 (MTCC 5314) providing initial cell concentration of 5.5 g/l in batch mode for 6 days. The temperature was maintained at 45° C. and stirred by magnetic stirrer at 50 rpm. 10 ml of fermentation broth was withdrawn at regular interval of 24 hr and analyzed for determination of residual starch by gram iodine method and ethanol concentration in the broth similarly as mentioned in previous examples. Overall yield of ethanol based on consumption of total starch was 22% of theoretical yield in the batch fermentation process in 6 days by the thermophilic strain *Kluyveromyces* sp. IIPE453 (MTCC 5314) achieving a productivity of 0.62 gl$^{-1}$d$^{-1}$.

The main advantages of the present invention are:
1. The yeast strain *Kluyveromyces* sp. IIPE453, MTCC 5314, capable of utilizing hexose and pentose sugars in sugar cane bagasse as carbon substrate simultaneously for growth at higher temperature range of 37 to 55° C. with a shorter lag phase of 4 hrs and high specific growth rate of 0.18 h$^{-1}$.
2. The yeast strain *Kluyveromyces* sp. IIPE453, MTCC 5314, can be used for the production of ethanol from low cost renewable biomass such as sugarcane bagasse or cassava starch as alternate feedstock to molasses.
3. The yeast strain *Kluyveromyces* sp. IIPE453, MTCC 5314, has the high stability in the continuous fermentation at high temperature.
4. High growth rate and ethanol production rate of the strain at higher temperature would be advantageous at lower process cost.
5. Application of the thermophilic yeast *Kluyveromyces* sp. IIPE453, MTCC 5314, has advantage of a more stable fermentation process by minimizing the chance of contamination with other mesophilic microorganisms.
6. Fermentation at high temperature facilitates the in situ recovery of ethanol, which eliminates the product inhibition.
7. In situ recovery of ethanol at high temperature increases the concentration of ethanol in condensate which reduces the cost of distillation.
8. The continuous process with cell recycle provides the high ethanol productivity and reuse of cells.
9. The recovery of acid from hydrolysate by ion exchange chromatography provides the recycling of acid for further hydrolysis of fresh biomass.

The invention claimed is:
1. A process for the preparation of ethanol by Kluyveromyces species IIPE453 MTCC 5314, comprising the steps:
    (a) culturing the strain Kluyveromyces species IIPE453 MTCC 5314 in salt medium 1 (SM1) wherein the said SM1 comprising 0.15 g/l di-sodium hydrogen ortho-phosphate, 0.15 g/l potassium di-hydrogen ortho-phosphate, 2.0 g/l ammonium sulphate, 1.0 g/l yeast extract and 10 g/l glucose with pH in the range of 5.0 to 6.5 at a temperature in the range of 37° C. to 55° C. for a period of 24 to 30 hours under stirring to obtain cell biomass;
    (b) inoculating the cell biomass as obtained in step (a) in fresh salt medium 2 (SM2) wherein the said SM2 comprises 0.15 g/l di-sodium hydrogen ortho phosphate, 0.15 g/l potassium di-hydrogen ortho phosphate, 1.0 g/l ammonium sulphate, 1.0 g/l yeast extract supplemented with 50 to 100 g/l of a fermentable substrate selected from the group consisting of monosaccharide and disaccharide sugars, bagasse, hydrolysate of lignocellulosic biomass, starch based biomass, either singly and in any combination thereof and with pH in the range of 3.5 to 6.5 at a temperature in the range of 45° C. to 60° C. for a period of 24 to 48 hours under stirring to obtain fermentation broth containing ethanol; or
    (c) immobilizing the cell biomass as obtained in step (a) onto bagasse chips and inoculating the immobilized biomass in fresh salt medium 2 (SM2) wherein the said SM2 comprises 0.15 g/l di-sodium hydrogen ortho phosphate, 0.15 g/l potassium di-hydrogen ortho phosphate, 1.0 g/l ammonium sulphate, 1.0 g/l yeast extract supplemented with 50 to 100 g/l of a fermentable substrate with pH in the range of 3.5 to 6.5 at a temperature in the range of 45° C. to 60° C. for a period of 40 to 90 hours under stirring to obtain fermentation broth containing ethanol; and
    (d) separating the ethanol from the fermentation broth.
2. The process according to claim 1, wherein the sugars are selected from the group consisting of glucose, maltose, xylose, sucrose and starch.
3. The process according to claim 1, wherein the concentration of fermentable substrate sugar in the medium SM2 is about 100 g/l.
4. The process according to claim 1, wherein the temperature of fermentation in step (b) is about 50 degree C. 50° C. to 55° C.
5. The process according to claim 1, wherein the pH in step (b) ranges from about 5.5 to about 6.0.
6. The process according to claim 1, wherein the productivity of ethanol ranges from about 0.78 to about 13.8 grams per liter per hour.
7. The process according to claim 1, wherein the yield of ethanol ranges from 10 to about 58.75%.
8. The process according to claim 1 wherein the separation of ethanol from fermentation broth in step (d) in done by a process selected from the group consisting of distillation, pre-evaporation and filtration.

* * * * *